United States Patent
Larsen et al.

(10) Patent No.: US 9,023,828 B2
(45) Date of Patent: May 5, 2015

(54) COMPOSITION COMPRISING AT LEAST ONE ALGINATE FOR USE IN TREATMENT AND/OR PREVENTION OF OVERWEIGHT

(75) Inventors: Finn Larsen, Hawick (DK); Brian Malm, Koge (DK); Jens Steen Olsen, Havdrup (DK)

(73) Assignee: S-Biotek af 15. Marts 2006 1 ApS, Køge (DK)

( * ) Notice: Subject to any disclaimer, the term of this patent is extended or adjusted under 35 U.S.C. 154(b) by 0 days.

(21) Appl. No.: 14/123,714

(22) PCT Filed: Jun. 1, 2012

(86) PCT No.: PCT/DK2012/050192
§ 371 (c)(1),
(2), (4) Date: Dec. 3, 2013

(87) PCT Pub. No.: WO2012/163366
PCT Pub. Date: Dec. 6, 2012

(65) Prior Publication Data
US 2014/0128342 A1    May 8, 2014

Related U.S. Application Data

(60) Provisional application No. 61/493,054, filed on Jun. 3, 2011.

(30) Foreign Application Priority Data

Jun. 3, 2011 (DK) .................................. 2011 70283

(51) Int. Cl.
*A61K 31/734* (2006.01)
*A23L 1/0532* (2006.01)
*A23L 1/29* (2006.01)
*A23L 1/308* (2006.01)

(52) U.S. Cl.
CPC .............. *A61K 31/734* (2013.01); *A23L 1/0532* (2013.01); *A23L 1/293* (2013.01); *A23V 2200/00* (2013.01); *A23L 1/308* (2013.01); *A23L 1/296* (2013.01)

(58) Field of Classification Search
CPC ............................ A61K 31/734; A23L 1/0532
USPC .......................................................... 514/54
See application file for complete search history.

(56) References Cited

U.S. PATENT DOCUMENTS

| 2003/0134027 | A1* | 7/2003 | Te Hennepe et al. | 426/590 |
| 2004/0228903 | A1 | 11/2004 | te Hennepe et al. | |
| 2005/0084592 | A1 | 4/2005 | Aldred et al. | |
| 2006/0222714 | A1* | 10/2006 | Aoyagi | 424/489 |
| 2007/0082025 | A1* | 4/2007 | Catani et al. | 424/439 |
| 2007/0082030 | A1 | 4/2007 | Aimutis et al. | |
| 2007/0082114 | A1 | 4/2007 | Catani | |
| 2010/0021495 | A1 | 1/2010 | Olsen | |
| 2010/0260904 | A1 | 10/2010 | Aimutis et al. | |
| 2012/0128734 | A1* | 5/2012 | Hubinette et al. | 424/400 |

FOREIGN PATENT DOCUMENTS

| EP | 1842544 A2 | 10/2007 |
| GB | 2324725 | 11/1998 |
| WO | WO03053169 A1 | 7/2003 |
| WO | WO2005020717 A1 | 3/2005 |
| WO | WO2005020719 A1 | 3/2005 |
| WO | WO2007044511 A1 | 4/2007 |
| WO | WO2007044611 A2 | 4/2007 |
| WO | WO2008098579 A1 | 8/2008 |

OTHER PUBLICATIONS

Larsen et al., Carbohydrate Polymers, 2003, 51, p. 125-134.*
Paxman et al., Appetite, 2008, 51, p. 713-719.*
International Search Report, and Written Opinion, PCT/DK2012/050192, mailed Aug. 10, 2012.
Sartori C. et al., "Determination of the cation content of alginate thin films by FTi.r. spectroscopy", Polymer, vol. 38, No. 1, pp. 43-51(1997).

* cited by examiner

*Primary Examiner* — Jonathan S Lau
(74) *Attorney, Agent, or Firm* — Winston & Strawn LLP

(57) ABSTRACT

The present invention relates to a composition in the form of a powder or a viscous paste, and which includes at least one low viscosity alginate having a viscosity of less than about 100 mPaS in a 1 wt % aqueous solution, and at least one high viscosity alginate having a viscosity of more than about 100 mPaS in a 1 wt % aqueous solution. The composition can also include at least one suspending agent. The composition is readily soluble in water such that an aqueous preparation can be prepared without substantive mixing. Also, the aqueous preparation is suitable for use in the treatment and/or prevention of overweight for both therapeutic and non-therapeutic purposes.

27 Claims, 3 Drawing Sheets

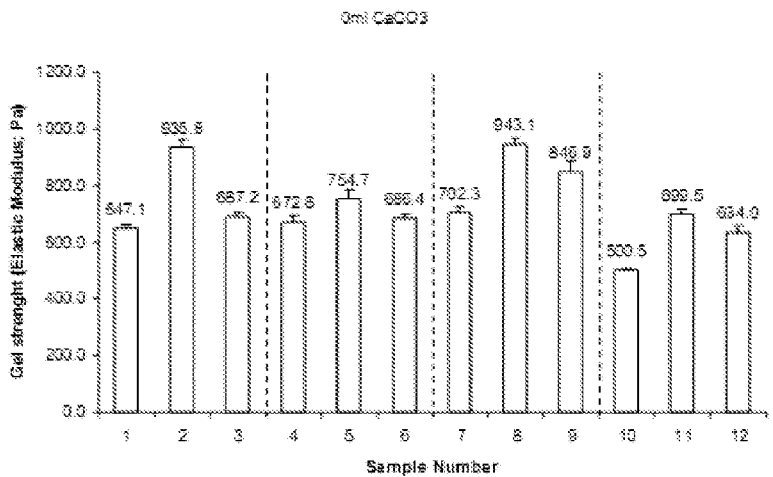
Fig. 1: Gel strength (Pa) of combinations of alginates number 1-12 w/ start solution 100ml no calcium added. Data are given as mean ± sd. See Table 1 for sample number description.
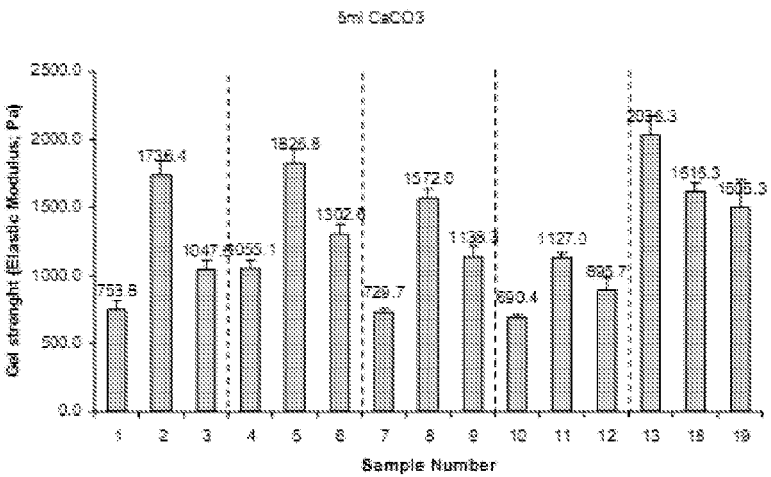
Fig. 2: Gel strength (Pa) of combinations of alginates number 1-19 w/ start solution 100ml + 5ml calcium added. Data are given as mean ± sd. See Table 1 for sample number description.

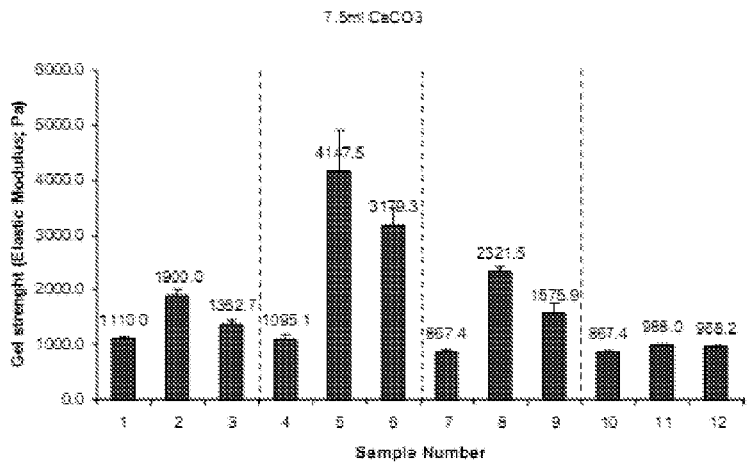

Fig. 3: Gel strength (Pa) of combinations of alginates number 1-12 w/ start solution 100ml + 7.5ml calcium added. Data are given as mean ± sd. See Table 1 for sample number description.

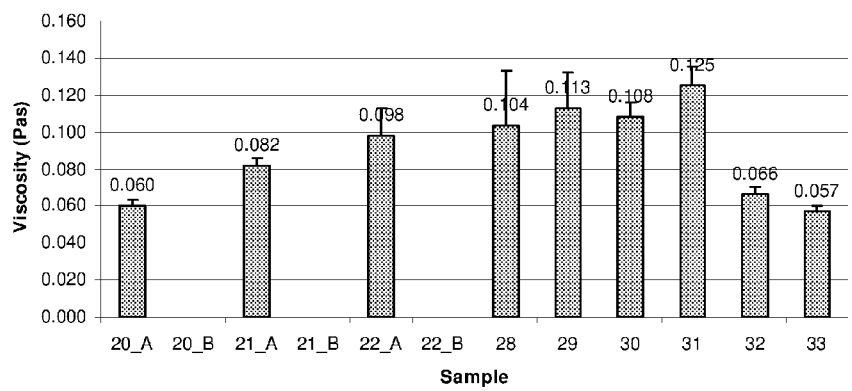

Fig. 4: Viscosity (Pas) of "ready to drink" alginate solutions with added calcium (2ml or 5ml), and sucrose (registered at mean shear rate 1-10 (1/s) and pH of ~6). Data are given as mean ± sd. See Table 2 and 3 for sample number description.

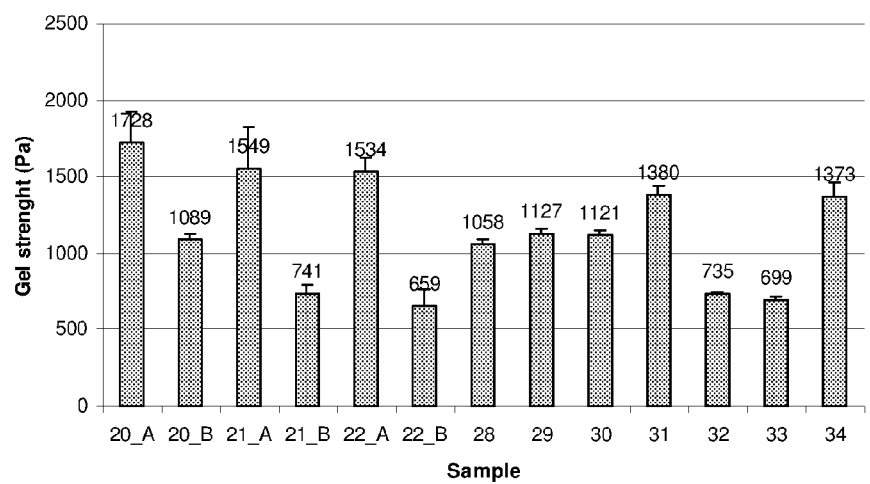
Fig. 5: Gel strength of different alginate combinations + 2ml (test_B) or 5ml (test_A) of 5%CaCO$_3$ solution. Data are given as mean ± sd. See Table 2 and 3 for sample number description.

COMPOSITION COMPRISING AT LEAST ONE ALGINATE FOR USE IN TREATMENT AND/OR PREVENTION OF OVERWEIGHT

This application is a 371 filing of International Patent Application PCT/DK2012/050192 filed Jun. 1, 2012, which claims the benefit of application no. 61/493,054, filed Jun. 3, 2011 and priority to Danish application no. PA 2011 70283 filed Jun. 3, 2011 and.

BACKGROUND

The present invention relates to a reconstitutable composition comprising at least one alginate, an aqueous diet preparation comprising said composition and the use of the aqueous diet preparation for the treatment and/or prevention of overweight for both therapeutic and non-therapeutic purposes.

The number of people affected by overweight and obesity continues to rise along with the prevalence of comorbidity diseases that result from this condition.

However, the effective treatment of obesity remains a largely unachieved goal. Many studies indicate that the main causes of obesity are bad nutrition and lack of physical activity. Therefore, in order to prevent obesity it is necessary for people to change both their eating behaviors, to achieve a desired change in body weight, and include physical activity in their lifestyles.

In order to achieve a weight loss in relation to a diet plan, the main objective is to reduce the caloric intake on a daily basis, however, in order for an individual to be able to follow a diet, it is important that the individual does not feel hunger nor the complications normally associated with hunger, e.g. faintness. In this respect, foods containing strong-gelling fibers may provide a safe and efficacious strategy for reducing food and thereby caloric intake by stimulating the endogenous satiety signaling. Presently, one of the most promising fibers for this purpose is alginate.

Alginate is a non-digestible polysaccharide and can as such be classified as a dietary fibre. Dietary fibers have a range of physiological benefits and studies have shown that dietary alginates exhibit many of these. There is an improvement in GI barrier function and a reduction in the damaging potential of the luminal contents with changes in the colonic microflora. Dietary alginates reduce intestinal nutrient absorption and promote satiety both of which have implications for the control of Type II diabetes and obesity. (Brownlee et al., 2005 I. A. Brownlee, A. Allen, J. P. Pearson, P. W. Dettmar, M. E. Havler and M. R. Atherton et al., Alginate as a source of dietary fiber, *Critical Reviews in Food Science and Nutrition* 45 (6) (2005), pp. 497-510. View Record in Scopus/Cited By in Scopus (28).

Alginates have a wide range of uses, reflecting the diverse heterogeneous nature of these naturally-occurring polymers. They are widely used in the food and textile industries as thickeners, stabilizers, gel-formers, film-formers etc. Alginates, which have GRAS status (General Recognised As Safe) also have a wide range of uses in the pharmaceutical, healthcare and dental arena (Onsoyen, 1996 E. Onsoyen, *Commercial applications of alginates, Carbohydrates in Europe* 14 (1996), pp. 26-31).

Recently, the role of alginates in pharmaceutical and food applications, and in relation to human health has broadened recently with the recognition that they have a number of potentially beneficial physiologically effects in the gastrointestinal tract.

These include an effect on intestinal absorption and colonic health. Importantly, alginates have also been shown to moderate human appetite and energy intake.

The formation of alginate gels can either be obtained due to the presence of multivalent cations e.g. in the form of calcium (ionic gelation) or alternatively be obtained when the pH is less than 3.5 (acid gelation). It has been proposed that, following ingestion, ionic gelation of alginate in stomach acid, i.e. gelation in the presences of cations, can modulate feeding behavior through slowed gastric clearance, promoting a feeling of endogenous satiety by stimulation of gastric stretch receptors and attenuated nutrient uptake.

A number of documents describe food products comprising alginates, which undergo ionic gelation in the stomach and thereby produce a feeling of satiety.

One examples of such a food product is known from WO 2003/053169. Said document discloses a liquid edible composition containing pectin or alginate together with a calcium salt which is insoluble at neutral pH. The calcium salt will dissolve in the stomach under the influence of the pH reduction. The increasing calcium concentration will stimulate the pectin and/or alginate gel-formation as calcium ions and the polysaccharides form a rigid matrix.

Similar, WO 2005/020717 and WO 2005/020719 relate to a food product, which in addition to alginate and insoluble calcium salt also comprises protein. The food product may be a liquid or a spoonable edible product.

Calcium-induced gel-formation requires that a high amount of calcium salt must be present in the product before consumption. In the drinks known from to US 2004/0228903, WO 2005/020717, WO 2005/020719 and US2010/0260904 the calcium salt is present as an insoluble or otherwise protected salt, i.e. a salt that first becomes soluble when a pH value corresponding to the pH-value in the stomach has been reached.

The application, WO 2008/098579 relates to shelf-stable satiety enhancing liquid compositions comprising an alginate. Said liquid composition will upon ingestion, gel in the strongly acidic environment that prevails in the stomach. WO 2008/098579 discloses that the preferred gel-formation is obtained without the use of calcium ions. Furthermore, if calcium ions are present, only calcium salts, which are insoluble at neutral pH values, are contemplated.

The inventors have now discovered that a gel obtained without the use of calcium ions are not sufficiently strong to be able to be maintained in the stomach for a sufficiently long duration of time to provide the desired degree of satiety.

Furthermore, it is well-known that in order for an aqueous preparation to meet the acceptance of a general consumer the aqueous preparation shall not only have an agreeable appearance, e.g. have a low viscosity, be clear and without sedimentation and lumps but also have a pleasant smell and taste.

Alginates are conventionally associated with a fishy smell and odor coming from the seaweed from which they are extracted, and all the known aqueous preparations have to contain a number of flavor additives in order to conceal the unpleasant organoleptic properties of the alginates. However, addition of flavor additives are not always desirable, as said additives often have a negative impact on the viscosity of the aqueous preparation, i.e. the viscosity becomes too high before the preparation has been consumed.

A further problem with the prior art aqueous preparations is that the insoluble calcium salts present in such a preparation will precipitate and/or dissolve during storage resulting in the preparation having an unpleasant appearance.

Apart from the inconvenience of shaking the drink before consumption a heterogeneous product furthermore has the disadvantage that the consumer may either not obtain the calcium salt in a proper dose for an optimal gel formation to take place, or if the gel strength is insufficient the physiological stimulation of a feeling of satiety may not be obtained. Furthermore, the calcium salt will initiate the gel formation before consumption resulting in an unacceptable high viscosity.

The quantity of the soluble alginates, which will dissolve in water, is considered to be limited by the physical nature of the solutions rather than the actual solubility. As the concentration of alginate increases the solution passes through stages from a viscous liquid to a thick paste; at which point it becomes very difficult to disperse further alginate successfully. This is a well-known problem; see e.g. WO 03053169, which discloses that it is not possible to add high concentrations of alginates to aqueous preparations, as the beverage will reach an unacceptable high viscosity before consumption.

As described above, alginates have been used to prepare several different compositions to modulate appetite and energy intake. However, these documents are all describing alginate formulations that undergo ionic gelation upon reaction with gastric acid as they are using an acid-soluble calcium source to form the desired alginate gel, and in the presence of divalent cations such as calcium ions, it has conventionally not been possible to ensure a stable aqueous solution having a consisting low viscosity before consumption.

This is due to the fact that the guluronic segments of alginate chains are able to adopt the form of a buckled ribbon, and these segments can associate with the calcium ions to form aggregates similar to an "egg-box". Within these junction zones the alginate chains are in a regular pleated structure, which is stabilized by the calcium ions, each neutralizing a negative charge on two different chains. As a result, alginates richer in these guluronic blocks form stronger gels.

One solution to this problem could be to use alginates having a few guluronic segments, however, this will also provide weaker gels in the stomach with the result that the desired feeling of satiety cannot be obtained and maintained for a sufficient long period of time.

An additional problem when making aqueous preparations containing alginates is to obtain a solution, which is homogeneous and has a pleasant appearance; otherwise the consumer will not consider such a solution acceptable for consumption.

One of the problems with obtaining a homogenous solution and at the same time maintaining a low viscosity of the product before consumption is the hydrophilic nature of the alginates, which conventionally makes them useful as thickening agents, but leads to a number of difficulties when the alginates are to be dissolved in water.

When an alginate is dissolved in an aqueous preparation, the acid groups of the alginate are ionized and a viscous solution is obtained. With high viscosity and shear-thinning properties, its rheology is typical of solutions of flexible coil macromolecules. These two properties are proportional to the concentration and the molecular weight of the alginates. As the temperature rises, the viscosity decreases. This is reversible. Furthermore, when the alginates are solubilised, the alginates negatively charged carboxyl groups cause the straight alginate chains to repel each other and results in a stable aqueous solution. Such aqueous solution has smooth long-flow properties with Newtonian behavior.

Furthermore, even though alginates generally are considered to be soluble in water, a poor dispersion in water will occur if an alginate is added too rapidly to the water, i.e. producing pasty, floury lumps wetted on the outside, only. Thus, when an aqueous preparation is reconstituted from a powder, as suggested in WO 2003/053169, said preparation can only be prepared after a high-shear mixing for a relatively long duration, e.g. by blending the mixture for more than 30 minutes. The purpose of high-shear mixing is to prevent the particles to clump together, and become tacky as soon as the surface is hydrated. Powdered alginate is slowly poured into the upper part of a vortex created in the water by high-speed blender, which preferably must remain submerged to avoid too much aeration. If clumps form, the shear is often not sufficient to break them up. This is due to the tendency of the individual alginate particles in the powder to undergo surface swelling, i.e. they will stick to each other forming small aggregates of the partially swollen granules, generally with air trapped inside. Such aggregates, or "lumps," are very difficult to disperse because the entrapped bubbles resist the penetration of water, and therefore, it is difficult for water to penetrate into the interior of a lumpy aggregate.

Use of coarse particles can be preferred in order to circumvent these problems, because they are easier to disperse and keep separate, however, such particles will be slower to dissolve compared to smaller particles, which will dissolve more rapidly. However, as mentioned above there is a substantial risk of the smaller particles to clump together and thereby preventing efficient solution and dispensation.

Accordingly when alginates in dietary products have been added to aqueous products as dry powders, it is very difficult to dissolve the alginates in water, and it has been proven to be a time-consuming task requiring excessive mixing.

Thus there is a demand for an aqueous diet product, which can be prepared in an easy, simple and reliable manner from e.g. a powder without requiring vigorous mixing, and at the same time ensuring that the final product meets the consumer's demands to organoleptic properties, i.e. the aqueous preparation must be homogenous, clear and have an acceptable low viscosity.

Therefore, it is a first aspect according to the present invention to provide a composition containing at least one alginate, which can be readily dissolved in an aqueous preparation, A second aspect of the present invention is to provide an aqueous diet product which is homogenous, clear and with a low viscosity, and at the same time has a pleasant smell and odor, and A third aspect of the present invention is to provide an aqueous diet product that can be used both to treat and/or prevent overweight in therapy and/or for the cosmetic treatment and prevention of overweight, i.e. losing weight.

The novel and unique features whereby these and further aspects are achieved is the fact that the invention relates to a reconstitutable composition in the form of a powder or a viscous paste, said composition comprises at least one low viscosity alginate having a viscosity of less than about 100 mPaS in a 1 wt % aqueous solution and at least one high viscosity alginate having a viscosity of more than about 100 mPaS in a 1 wt % aqueous solution.

As used herein "low viscosity alginates" means those alginates having a viscosity of less than about 100 mPaS in a 1 wt % aqueous solution when determined on a Brookfield viscometer model LV using spindle No 2 at 60 rpm at 20° C.

Similar as used herein "high viscosity alginates" means those alginates having a viscosity of more than about 100 mPaS in a 1 wt % aqueous solution when determined on a Brookfield viscometer model LV using spindle No 2 at 60 rpm at 20° C.

SUMMARY OF THE INVENTION

Surprisingly, the inventors have found that using a combination of a low viscosity alginate and a high viscosity alginate, the provided composition will be readily soluble in water, such that the composition easily can be used to prepare an aqueous preparation without substantive mixing. Furthermore, as humans cannot degrade alginates such an aqueous preparation will also have a very low caloric content, and therefore be suitable for use in the treatment and/or prevention of overweight for both therapeutic and non-therapeutic purposes.

The obtained aqueous preparation is directly suitable as an aqueous diet product, which due to the unique combination according to the invention has an agreeable appearance for the consumer i.e. the aqueous preparation will have a low viscosity, be clear, without sedimentation and lumps and also have a pleasant smell and taste.

In this respect the composition according to the invention is provided as a reconstitutable preparation, preferably accompanied with instructions to reconstitute the preparation into a suitable liquid, e.g. water, prior to consumption. The term "reconstitutable preparation" as used herein refers to a preparation that needs addition of a suitable liquid prior to ingestion.

BRIEF DESCRIPTION OF THE DRAWINGS

FIG. 1 illustrates Gel strength (Pa) of combinations of alginates number 1-12 w/ start solution 100 ml no calcium added. Data are given as mean ±standard deviation. See Table 1 for sample number description.

FIG. 2 illustrates Gel strength (Pa) of combinations of alginates number 1-19 w/ start solution 100 ml +5 ml calcium added. Data are given as mean ±standard deviation. See Table 1 for sample number description.

FIG. 3 illustrates Gel strength (Pa) of combinations of alginates number 1-12 w/ start solution 100 ml +7,5 ml calcium added. Data are given as mean ±standard deviation. See Table 1 for sample number description.

FIG. 4 illustrates Viscosity (Pas) of "ready to drink" alginate solutions with added calcium (2 ml or 5 ml), and sucrose (registered at mean shear rate 1-10 (1/s) and pH of 6. Data are given as mean ±standard deviation. See Tables 2 and 3 for sample number description.

FIG. 5 illustrates Gel strength (Pa) of different alginate combinations +2 ml (test_B) or 5 ml (test_A) of 5% $CaCO_3$ solution. Data are given as mean ±standard deviation. See Tables 2 and 3 for sample number description.

DETAILED DESCRIPTION OF THE INVENTION

In addition to water, the liquid can be any suitable liquid, preferable a low-food-energy liquid, e.g. skimmed milk.

Since the acidic environment in the stomach causes the alginates of low viscosity, in the aqueous preparation, to become a thick gel in the stomach, the consumer will subsequently experience a feeling of satiety. Furthermore, it is likely that this gel has an active function in retaining fat, thereby reducing their uptake in the stomach or bowel. Thereby, some food constituents, incl. fat, can pass undigested. Passage through the stomach and bowel is regulated by the aqueous preparation according to the invention as a prolonged time of gastric emptying of consumed foods is observed after intake of the aqueous preparation.

Without being bound by theory, it is believed that it is the low viscosity alginate, which ensures the relatively high degree of solubility observed for the composition according to the invention, whereas the high viscosity alginate ensures that a sufficient thick and strong gel is obtained in the stomach of the consumer in order to provide the sensation of satiety. It must be noted that test using compositions without one of the compounds in the composition according to the invention provided aqueous preparation, which was either too viscous before consumption (compositions without low viscosity alginate) or preparations which did not have a sufficient viscosity and gel strength after consumption (compositions without high viscosity alginate).

Furthermore, due to the composition according to the invention smaller amount of alginates are required than hitherto known in order to obtain the desired gel strengths in the stomach.

Furthermore, the inventors have found that if at least one low viscosity alginate has a viscosity of less than about 40 mPaS in a 1 wt % aqueous solution this will further improve the solubility of the composition.

In this respect it is preferred that the composition according to the invention comprises at least two low viscosity alginates and wherein at least one of said alginates has a viscosity below 40 mPaS in a 1 wt % aqueous solution, or optionally three low viscosity alginates, wherein at least two of said alginates has a viscosity below 40 mPaS in a 1 wt % aqueous solution.

In a preferred embodiment the composition according to the invention comprise at least two high viscosity alginates, as the inventors have found that using different high viscosity alginates further improves the gel stability and strength.

In order to ensure both a high solubility and a large gel stability and strength, the preferred ratio of the weight of the at least one low viscosity alginate to the weight of the at least one high viscosity alginate in the composition is about 1:1 to 10:1, more preferably 1.5:1 to 2:1, preferably about 1.72:1 to 1.75:1.

In order to ensure a fast and complete dispersion of the alginate in the liquid the composition according to the invention can further comprise at least one suspending agent.

In the present context the term "suspending agent", means any agent capable of providing the desired solubility and/or dispersibility of the alginate containing composition, i.e. is capable of providing an aqueous preparation with is substantially clear and without sedimentation and lumps. This is e.g. achieved when the composition according to the invention after addition to water is either dissolved or broken down into smaller particles passing through a 150 μm sieve. Without being bound by theory it is believed that the suspending agent ensures that the alginate particles are diluted and separated helping to keep the alginate particles apart, as they are wetted. It is preferred that the suspending agent is in the form of a particulate material, as this has proven to provide the best result.

The ratio of the alginate to the suspending agent in the composition is preferably about 0.5:1 to 10:1, more preferably 1:1 to 2:1 as the inventors have shown said ratios provides the best solubility/dispersibility.

A preferred suspending agent is selected from the group consisting of erythritol, inulin, polydextrose, dextrin, oligofructose, sucrose, succrine, Perfect Fit®, sucrose, tagatose or combinations thereof. Similar suspending agents are also contemplated within the scope of the present invention.

In order to ensure a fast dispersion of the alginate in the liquid, preferably water, it is preferred that the composition according to the invention has a high solubility/dispersibility in water. Said solubility is as stated above 10 mg/ml water at pH 7 and 20° C., however it is preferred that an even higher solubility is provided for said composition, e.g. above 20 mg/ml water at pH 7 and 20° C. and more preferably above 30 mg/ml water at pH 7 and 20° C. The larger the solubility the faster the composition will be dissolved/dispersed within the water.

In the context of the present invention the term "solubility" means the property of the composition to dissolve and/or disperse in a liquid solvent to form a homogeneous solution of the alginate. As an example can be mentioned that said solubility is achieved when the composition according to the invention after addition to liquid is either dissolved or broken down into smaller particles capable of passing through a 150 µm sieve.

In order to ensure that the gel obtained in the stomach is sufficiently strong to be able to be maintained in the stomach for a sufficiently long duration to provide the desired degree of satiety the inventors have shown that this is easily obtained, when calcium ions are present during the gel formation. In this respect, it is preferred, that the composition according to the invention further comprises between 0.1 and 20 wt % of a calcium salt based on the weight of the total composition according to the invention.

Any kind of calcium salt can be used in the present invention, and preferred is a calcium salt, selected from a group consisting of calcium phosphate, calcium carbonate, calcium sulfate, calcium oxide, calcium citrate, and calcium chloride. Within the scope of the present invention, any kind of alginate can be used and suitable sources of alginate include seaweeds and bacterial alginates. Preferably, sodium alginate and potassium alginate are used as a source of alginate. However, it is preferred to provide a powder or viscous paste, which is capable of producing an aqueous diet product, which after mixing with water, still has a viscosity low enough for consumer acceptance.

Therefore, according to an embodiment of the invention, it is preferred that the alginate used in the composition is selected to be of the kind which will not form a gel in the presence of calcium ions at pH 7, thus the alginates are preferably selected to undergo acid geletion, meaning that irrespectively of whether or not calcium ions are present in the composition or in the water used to dissolve said composition, the obtained diet product will have a viscosity, which will not affect consumer acceptance, by providing an unacceptable mouth-feel and reduced fluid replenishment. Without being bound by theory the inventors believe that acid gelation is obtained at pH-values below 3.5 as a steadily increasing number of carboxyl ions on the alginate chains become protonated with decreasing pH, reducing the electrical repulsion between chains. The chains can then move closer together, which allows hydrogen bonding to be more effective. At first this produces a higher viscosity and eventually, at pH 3.5-4.0, a gel is formed.

Surprisingly, the inventors have found that addition of calcium ions to alginate which undergoes acid gelation not only provides a stronger and more stable gel; but also a higher gel weight in comparison to acid gelation without addition of calcium ions. Thus, the composition according to the invention will not only lead to increased viscosity of stomach contents inducing a feeling of satiety but will also increase the period of time, which the gel stays in the stomach.

Alginates are polysaccharides that provide the main structural component of brown algae (seaweeds). Alginates are linear copolymers of (1-4) linked β-d-mannuronic acid (M) and α-l-guluronic acid (G). The distribution of M and G in alginate chains gives rise to three different block types, namely blocks of poly-M, blocks of poly-G and alternating MG blocks. The chemical composition of alginate is variable according to the seaweed species, within different parts of the same plant (stem or leaf), seasonal changes and the conditions of the sea.

The affinity for cations and the gel forming properties of the alginates are mostly related to the content of G residues, as when two G residues are adjacent in the polymer they form a binding site for polyvalent cations (O. Smidsrod and K. I. Draget, *Chemistry and physical properties of alginates, Carbohydrates in Europe* (1996), pp. 6-13. Smidsrod & Draget, 1996).

In one embodiment the low viscosity alginate has a ratio of mannuronic acid to guluronic acid (M/G) of less than 1, suitably as low as 0.7 and even more preferably as low as 0.5, as it has been found that an alginate with a larger amount of guluronic acid compared to mannuronic acid has improved gelling properties upon lowering the pH, in the absence of cross-linking metal ions such as calcium ions. Preferably the amount of guluronic acid is above 60% and the amount of mannuronic acid is below 40% of the total content of alginate.

Similar it is preferred that the ratio of beta-D mannuronic acid to alpha-L guluronic acid in the high viscosity alginates is equal to or above 1.

Combining low viscosity alginates having a M/G ratio of less than 1, and high viscosity alginate having a M/G ratio above 1 has proven to be especially advantageously in order to provide the desired effects of the composition according to the invention, i.e. the composition will be readily soluble in water, such that the composition easily can be used to prepare an aqueous preparation without substantive mixing. The obtained aqueous preparation has a low viscosity, is clear and without sedimentation and lumps and is capable of increasing the viscosity of stomach contents inducing a feeling of satiety and at the same time increase the period of time, which the gel stays in the stomach.

The solubility of the alginates decreases with an increase in molecular weight, however, surprisingly the inventors have discovered, that with the composition according to the invention, it is also possible to dissolve alginate molecules having a relatively large molecular weight. In this respect it has been found possible to dissolve alginates having a weight around 300.000 Da, which previously has been considered almost impossible. Using alginates having a larger molecular weight further provides the benefit that lower concentrations of alginates are required in order to obtain the desired degree of satiety and such alginates will also exhibit both good gelling properties and high gel weights.

In order to provide an aqueous diet product, which does not have the fishy smell associated with conventional alginates, it is desired to use alginates overall free of smell or taste, ensuring that they can be formulated in any aqueous solution, including pure water, without any addition to its own taste. Methods for quantifying odors and taste are well known in the art and will not be disclosed in further details, however as an example it can be mentioned that an olfactometer is used to detect and measure odor, and normally used in conjunction with human subjects in laboratory settings to quantify and qualify human olfaction.

Suitable low viscosity alginates for the composition according to the invention can preferably be selected from the group consisting of Manugel® GHB, Protanal® GP 1740, Protanal® LF 5/60, Protanal® LFR 5/60, Manugel® LBA and similar pharmaceutical or non-pharmaceutical grade alginates. Suitable high viscosity alginates can preferably be selected from the group consisting of Manugel® GMB, Protanal® GP5450, and Protanal® SF 120 RB and similar pharmaceutical or non-pharmaceutical grade alginates.

If one or more of the low or high viscosity alginate used in the composition according to the invention undergo ionic gelation at pH 7 it is preferred that a calcium salt is not added to the composition according to the invention, as this will result in a high viscosity of the aqueous preparation before consumption. As an example of a high viscosity alginate which undergoes ionic gelation can be mentioned Manugel® DMB available from FMC Biopolymer.

In such cases it is preferred that the calcium salt is placed in a separate composition, which can be consumed either before or after the aqueous preparation. This will provide a physical separation of the calcium ions from the alginate ensuring that the alginates do not form a gel until after both components are allowed to react with each other in the stomach. In this respect it is preferred to provide a kit comprising both the composition according to the invention and a separate calcium containing composition. Said kit is preferably accompanied with instructions to reconstitute the preparation into a suitable liquid, e.g. water prior to consumption as well as information that the calcium composition, shall be ingested either shortly before or after the consumption of the aqueous preparation. The calcium composition can have any desired form and both be a reconstitutable powder to be dissolved in liquid, e.g. water or alternatively a tablet, pill or capsule. The type of composition is not important as long as the calcium ions are readily available in the stomach.

When the calcium salt is provided as a separate calcium composition it is preferred that the calcium salt has a solubility of at least 5 mg per ml at 20° C. and pH 7, ensuring that the calcium ions are readily available in the stomach. All the formulations known in the prior art rely on endogenous gastric acid to trigger the solubility of the calcium salt, however, since gastric pH is not a consistent factor and varies among individuals, e.g. due to meal consumption, time and medication usage, it is advantageously if the calcium ions are immediate available when the composition reaches the stomach, and using a calcium salt having a good solubility ensures that the calcium ions do not become the limiting factor during gel formation. In this respect calcium chloride have proven to be especially useful, as said salt already are accepted for human consummation, however other calcium salt having similar properties are also contemplated within the scope of the invention.

As the composition according to the invention is intended for use as an "over the counter" composition with the intention of helping humans during weight loss, the composition according to the invention will in a preferred embodiment not comprise any active pharmaceutical ingredients, i.e. substances normally placed in a pharmaceutical drug and which is considered to be the biologically active ingredients.

The composition according to the invention can either be a dry powder or alternatively a viscose paste/dispersion in which the alginates are already wetted preferably with water. It is preferred that enough liquid is added to said paste to give a pourable slurry as this in some embodiments can ensure that the alginate particles are even more easy dispersed.

In a preferred embodiment the composition according to the invention also comprises at least one nutritional component selected from the group of: a protein source, a lipid source, a carbohydrate sources, and vitamins, and minerals components. It is preferred that the concentration of said nutritional component(s) is nutritionally balanced such that the composition according to the invention meets the recommended daily requirements for vitamins, minerals, trace elements, fatty acid and protein, thus when the composition is mixed with a suitable liquid the resulting aqueous preparation is a meal replacement. Said meal replacement can e.g. be a conventional meal replacement, a low calorie diet (LCD) product or a very low calorie diet (VLCD) products. VLCD is a diet with very or extremely low daily food energy consumption, and is defined as a diet of 800 kcal per day or less, were a LCD is defined as a diet of about 1000 kcal per day.

The specific amounts of the individual nutritional components are well known by those skilled in the art and can be readily calculated when preparing such products. Such meal replacement products can serve as the sole source of nutrition, or the consumer can consume such products to replace one or two meals a day, or to provide a healthy snack. The aqueous products according to the invention should be construed to include any of these embodiments.

According to the present invention, the concentration of the alginate in the composition is dosed to fulfill desired requirements.

As an example can be mentioned, that in a first dosage unit to be dissolved in about 500 ml liquid e.g. water, the amount of alginate in the composition according to the invention, is preferably between 2 and 8 g, preferably between 4 and 6 g alginate and more preferably between 4.5 and 5.5 g alginate.

The inventors have discovered that in a preferred embodiment the composition according to the invention comprises about 1.45 g Manugel® GMB; about 1.45 g Manugel® GHB, about 1.5 g Protanal® GP1740, about 0.25 g Protanal® LF 5/60, about 0.5 g Protanal® GP5450 and about 3 g erythritol. However, variations and modifications of said composition is contemplated within the scope of the present invention.

As a different example can be mentioned that in a dosage unit to be dissolved in about 300 ml to about 350 ml liquid, e.g. water, the amount of alginate in the composition according to the invention, is preferably between 0.5 and 3 g, preferably between 1 and 2 g alginate and more preferably about 1.5 g alginate. Such a unit dosage is especially applicable for being used for aqueous preparations intended for being used as a meal replacement, i.e. where the aqueous product also comprises the required nutritional components for providing a balanced nutritional meal for the consumer, but the aqueous product according to the invention can equally well be prepared without such components, and be used as a product intended for providing a sufficient degree of satiety.

An example of the specific composition for being dissolved in about 300 ml to about 350 ml liquid is a unit dosage comprises about 0.48 g Manugel® GMB; about 1 g Protanal® GP1740, and about 0.1 g Protanal® GP5450.

In a further example were the dosage unit is intended for being dissolved in about 500 ml liquid, e.g. water, the amount of alginate in the composition according to the invention, can preferably be between 1 and 5 g, preferably between 2 and 4 g alginate and more preferably about 3 g alginate. Said unit dosage is especially applicable for being used in an aqueous product which is intended for being used in the treatment or prevention of overweight or obesity in therapy and/or for the cosmetic treatment or prevention of overweight.

A preferred unit dosage intended for being dissolved in about 500 ml liquid comprises about 0.96 g Manugel® GMB; about 2 g Protanal® GP1740, and about 0.2 g Protanal® GP5450.

In order to ensure a strong and stable gel the unit dosage may further comprise about 500 mg calcium, e.g. in the form of a calcium salt having a relatively high solubility. Alternatively the composition can comprise about 1.25 g calcium carbonate. The calcium salt can either be part of the composition according to the invention or be separate to the composition.

As described the composition according to the invention can be used to prepare an aqueous diet product designed to undergo enhanced acid gelation in the stomach, i.e. a gelation which preferably is dependent of gastric acidity, as the calcium ions are readily available.

In order to obtain a sufficient feeling of satiety the concentration of alginate in the final product is preferably between 0.3 wt % and 1.6 wt %, more preferably between about 0.5 and about 0.9 wt %. Furthermore, in order to ensure sufficient gel strength, gel weight and gel stability the calcium salt are preferably present in a concentration between 0.1 wt % and 3 wt %.

It is important that the calcium salt does not provide a final aqueous preparation with a salty aftertaste, therefore in some situations it can be preferred that the calcium salt is present in a concentration below or around 0.5 wt %.

Furthermore, since bottom sedimentation after mixing the composition with water is eliminated using the comparison according to the invention, the undesirable drawbacks previously associated with alginate containing beverages is eliminated and an aqueous preparation which is pleasant, acceptable and without a fishy smell and odor is provided, thereby increasing consumer acceptability of said aqueous preparation compared to alginate containing drinks described in the prior art.

It is preferred that the composition according to the invention will not form a gel at neutral pH in the presences of calcium ions, meaning that the viscosity of the aqueous preparation is below 130 mPaS at a shear rate of $100\ s^{-1}$, $20°$ C. and pH 7, preferably below 110 mPaS and more preferably below 80 mPaS.

When the product reaches the stomach it is preferred that the viscosity of the aqueous diet product increases 20 times or more, when the intra gastric pH is decreased from around pH 7 to pH 2. In certain aspect, the increase of the viscosity is 50 times or more, such as 100 times or more.

Using the preferred embodiment according to the invention the viscosity of the aqueous diet product increases to at least 1200 PaS, preferably at least 1350 PaS, when the pH value is reduced from pH 7 to pH 2.

Even though it is desirable to obtain an increased viscosity, it is equally important to obtain a sufficient gel strength, as the gel formed in the stomach otherwise will be degraded too fast to ensure a prolonged feeling of satiety. In this respect it is desirable that the gel weight obtained after the pH value is lowered from pH 7 to pH 2, is above 90 g/100 ml water, more preferably above 93 g/100 ml water and even more preferably above 95 g/100 ml water, as an increase in gel weight is beneficial, also this has been proven not only to be beneficial in relation to a feeling of satiety but also in relation to a reduction of gastric emptying, stimulate gastric stretch receptors and reduce intestinal nutrient uptake and influence the glycemic response.

It was found that the present aqueous composition can suitably be used to induce satiety. Hence the present drink can be advantageously in a method for the reduction of the appetite in a human, said method comprising administering to said human an appetite reducing amount of the above described aqueous composition. The present method is preferably used to prevent and/or treat overweight in humans, even more preferably human adolescents. Furthermore, the present aqueous composition reduces caloric intake of a meal, when the drink is consumed shortly before or during the same meal. Hence the present invention also provides a method for reducing the caloric intake of a meal, for prevention of ingesting excess calories when ingesting a meal and/or controlling daily caloric intake, said method comprising administering to a human an effective amount of the aqueous drink as described above, shortly before or during the meal. The present method can both be used to treat or prevent overweight in therapy and/or for the cosmetic treatment or prevention of overweight, i.e. losing weight.

EXAMPLES

The purpose of the experiments mentioned below is to select a combination of alginates for use in the preparation of a aqueous preparation in an attempt to both provide a higher degree of solubility and reduce the total alginate concentration in the known aqueous preparations. As an example of known aqueous preparation see international patent application No. WO2008/098579.

Low viscosity alginates with M/G ratios <1 (Manugel® GHB, Manugel® LBA, Protanal® LFR 5/60) were combined with alginates of high viscosity with M/G ratios >1 (Manugel® GMB, Protanal® GP5450, Protanal® SF 120 RB, and Manugel® DMB) all provided by FMC Biopolymer (Philadelphia, USA).

As a suspending agent in the combinations was used either a sugar and fat substitute, 0.2-0.4% Perfect Fit® provided by Isis Aps (Viby J, Denmark) or erythritol or combinations thereof.

Methods
Preparing the Composition

The different alginates and erythritol were weighed on an electronic weight (Sartorius Analytic A2005, Germany) to the nearest third decimal (mg). Mixing took place in 100 ml disposable plastic cup on the magnetic stirring (KMO2 Basic IKA-Werke) with 500 rpm for 5 min until the composition was considered homogenous.

Preparing the Aqueous Preparation 500 ml demineralized water (Milli-Q Plus) was measured in a 700 ml plastic shaker provided and the different compositions were added. Thereafter, the mixture was shaken until the aqueous preparation was clear and in overall without sedimentation and lumps. In all cases this was obtained, within a period of 15 to 60 seconds. After preparation of all alginate solutions either 2, 5 or 7.5 ml of calcium carbonate solution (5 g $CaCO_3$/100 ml) (Sigma-Aldrich, Denmark A/S) was added. To relevant alginate solutions the flavor Mango Passion were added in the following ratio. To 500 ml alginate solutions were added 0.08 g aspartame, 6 g aroma Mango Passion, and 0.03 g Beta-carotene 7%.

Gel Formation

The prepared alginate solutions were placed on magnetic stirrer with stirring (600-800 rpm). For control of the pH value a pH meter (Metrohm Swiss model 691) was placed in the alginate solution. Thereafter 2 ml of 0.5 mol of HCl (hydrochloric acid) was added every 10 seconds until the pH value was 2 (~20 ml HCl in total).

Gel Strength

The oscillatoric shear rheology was performed on a Bohlin C-Vor rheometer (Malvern Instruments Ltd. UK) at constant shear rate (1 Hz). The actual stress amplitude varied 15 steps, where the mechanical stress was controlled and gradually increased from 0.08-100 (Pa=1 g·cm-1·s-1). Stress was applied for 12 sec. one time for each step and voltage amplitude was recorded, and the elastic (G') and viscous (G") modulus calculated. During oscillations measurements there were obtained a plateau in the elastic modulus. To achieve a single value for the gel mass strength, the mean of the elastic modulus between 0.2-10 shear stress in is used in this report.

Results

Table 1-4, shows a number of different compositions according to the invention, the amount of added calcium, added flavor and added suspending agent.

TABLE 1

| Sample | Protanal LFR5/60 g/100 ml | Manugel GMB g/100 ml | Manugel LBA g/100 ml | Protanal SF 120 RB g/100 ml | Perfect fit g/100 ml | Flavor | CaCO$_3$ [5 g CaCO$_3$/100 ml] |
|---|---|---|---|---|---|---|---|
| 1  | 0.6 | 0.5  |     |      |     | 0.4 | 0, 5, 7.5 ml |
| 2  | 1.0 | 0.5  |     |      |     |     | 0, 5, 7.5 ml |
| 3  | 0.8 | 0.5  |     |      |     | 0.2 | 0, 5, 7.5 ml |
| 4  |     | 0.5  | 0.6 |      |     | 0.4 | 0, 5, 7.5 ml |
| 5  |     | 0.5  | 1.0 |      |     |     | 0, 5, 7.5 ml |
| 6  |     | 0.5  | 0.8 |      |     | 0.2 | 0, 5, 7.5 ml |
| 7  | 0.3 | 0.5  | 0.3 |      |     | 0.4 | 0, 5, 7.5 ml |
| 8  | 0.5 | 0.5  | 0.5 |      |     |     | 0, 5, 7.5 ml |
| 9  | 0.4 | 0.5  | 0.4 |      |     | 0.2 | 0, 5, 7.5 ml |
| 10 | 0.3 | 0.25 | 0.3 | 0.25 |     | 0.4 | 0, 5, 7.5 ml |
| 11 | 0.5 | 0.25 | 0.5 | 0.25 |     |     | 0, 5, 7.5 ml |
| 12 | 0.4 | 0.25 | 0.4 | 0.25 |     | 0.2 | 0, 5, 7.5 ml |
| 13 | 1.0 | 1.0  |     |      |     |     | 5 ml |
| 18 | 0.5 | 0.5  | 0.5 |      |     | 0.4 | 5 ml |
| 19 | 0.3 | 0.6  | 0.3 |      |     | 0.3 | 5 ml |

Each sample number were formulated and measured two times.
Note:
samples 14-17 is not shown as they were investigated under different methods for gel formation (by GDL).

TABLE 2

| Sample | Manugel GMB | Manugel GHB | Manugel GP5450 | Manugel LBA | Erythritol | Flavor | Test: A Gel strength | Test: B Gel strength | Test: A Viscosity |
|---|---|---|---|---|---|---|---|---|---|
| 20 | 1.5 g (0.3 wt %) | 1.5 g (0.3 wt %) | 0.5 g (0.1 wt %) | 2.0 g (0.4 wt %) | 3.0 g (0.6 wt %) | 6.0 g (1.0 wt %) | +5 ml I CaCO$_3$* | +2 ml CaCo$_3$** | +5 ml CaCO$_3$ |
| 21 | 1.5 g (0.3 wt %) | 1.5 g (0.3 wt %) | 0.75 g (0.15 wt %) | 1.75 g (0.375 wt %) | 3.0 g (0.6 wt %) | 6.0 g (1.0 wt %) | +5 ml CaCO$_3$ | +2 ml CaCo$_3$ | +5 ml CaCO$_3$ |
| 22 | 1.5 g (0.3 wt %) | 1.5 g (0.3 wt %) | 1.0 g (0.2 wt %) | 1.5 g (0.3 wt %) | 3.0 g (0.6 wt %) | 6.0 g (1.0) | +5 ml CaCO$_3$ | +2 ml CaCo$_3$ | +5 ml CaCo$_3$ |

*5 ml of 5% CaCO$_3$ solution = 1.25 g CaCO$_3$ in a 500 ml beverage.
**2 ml of 5% CaCO$_3$ solution = 0.5 g CaCO$_3$ in a 500 ml beverage.
Note:
samples 23-27 is not shown as they were investigated under different methods for gel formation (by GDL).

TABLE 3

| Sample | Manugel GMB | Manugel GHB | Manugel DMB | Manugel LBA | Erythritol | Gel strength | Viscosity |
|---|---|---|---|---|---|---|---|
| 28 | 1.5 g (0.3 wt %) | 1.5 g (0.3 wt %) | 0.5 g (0.1 wt %) | 2.0 g (0.4 wt %) | 3.0 g (0.6 wt %) | +2 ml CaCO$_3$ | +2 ml CaCO$_3$ |
| 29 | 1.5 g (0.3 wt %) | 1.5 g (0.3 wt %) | 0.75 g (0.15 wt %) | 2.0 g (0.4 wt %) | 3.0 g (0.6 wt %) | +2 ml CaCO$_3$ | +2 ml CaCO$_3$ |
| 30 | 1.75 g (0.35 wt %) | 1.5 g (0.3 wt %) | 0.5 g (0.1 wt %) | 2.0 g (0.4 wt %) | 3.0 g (0.6 wt %) | +2 ml CaCO$_3$ | +2 ml CaCO$_3$ |
| 31 | 1.75 g (0.35 wt %) | 1.5 g (0.3 wt %) | 0.75 g (0.15 wt %) | 2.0 g (0.4 wt %) | 3.0 g (0.6 wt %) | +2 ml CaCO$_3$ | +2 ml CaCO$_3$ |
| 32 | 1.75 g (0.35 wt %) | 1.5 g (0.3 wt %) | 0 | 2.0 g (0.4 wt %) | 3.0 g (0.6 wt %) | +2 ml CaCO$_3$ | +2 ml CaCO$_3$ |
| 33 | 1.5 g (0.3 wt %) | 1.5 g (0.3 wt %) | 0 | 2.0 g (0.4 wt %) | 3.0 g (0.6 wt %) | +2 ml CaCO$_3$ | +2 ml CaCO$_3$ |

TABLE 4

| Sample | Manugel GMB g/100 ml | Manugel GHB g/100 ml | Protanal GP1740 g/100 ml | Protanal LF5/60 g/100 ml | Manugel GP5450 g/100 ml | Erythritol | Flavor | *calcium |
|---|---|---|---|---|---|---|---|---|
| 35 |       |       |     | 15   |       | 3.0 |   | 0.5 g CaCO$_3$ |
| 36 | 1.35  | 1.35  | 1.5 | 0.25 | 0.45  | 3.0 | + | 5 ml CaCO$_3$ |
| 37 | 1.275 | 1.275 | 1.5 | 0.2  | 0.425 | 3.0 | + | 5 ml CaCO$_3$ |

TABLE 4-continued

| Sample | Manugel GMB g/100 ml | Manugel GHB g/100 ml | Protanal GP1740 g/100 ml | Protanal LF5/60 g/100 ml | Manugel GP5450 g/100 ml | Erythritol | Flavor | *calcium |
|---|---|---|---|---|---|---|---|---|
| 38 | 1.275 | 1.275 | 1.5 | 0.2 | 0.425 | 3.0 | +<br>(−)<br>Citric acid | 5 ml $CaCO_3$ |
| 39 | 1.45 | 1.45 | 1.5 | 0.25 | 0.5 | 3.0 | + | 5 ml $CaCO_3$ |

*5 ml of 5% $CaCO_3$ solution = 1.25 g $CaCO_3$ in a 500 ml beverage.

Gel Strength of Alginate Combinations from Table 1

FIG. 1 shows the measurement of gel strength (elastic modul, Pa) recorded by oscillatory shear rheology. The measurement of alginate combinations without calcium showed that sample number 2 (Protanal® LFR 5/60+Manugel® GMB) and 8 (Protanal® LFR 5/60+Manugel® GMB+Manugel® LBA) had the highest gel strength, and sample number 11 the lowest gel strength when not combined with Perfect Fit (See Table 1 for sample number description).

After addition of 5 ml calcium carbonate the inventors found increased gel strength for all samples (see FIG. 2). The highest gel strength was found for sample number 2 (Protanal® LFR 5/60+Manugel® GMB), 5 (Manugel® GMB+Manugel® LBA) and 8 (Protanal® LFR 5/60+Manugel® GMB+Manugel® LBA). As can be seen from the table most samples comprising Perfect Fit® comprise a lower amount of alginate. However, the results from sample 18 which was formulated as sample 8 but included Perfect Fit®, shows similar gel strength. Therefore, the reason for the lower gel strength of samples including Perfect Fit® is due to the lower total amount of alginate in the samples with Perfect Fit®. The sample 13 has a higher content of Manugel® DMB (double the amount of samples 1-9) and it results in the highest gel strength.

Although sample 13 exhibits the highest gel strength the viscosity of the "ready-to-drink" formulation was measured to be between 200-250 mPas, which is higher compared to Protanal® LFR 5/60, Manugel® LBA alone. Thereby, the palatability of such a preload beverage formulation would be decreased. The viscosity of sample 2 and 5, with 5 ml $CaCO_3$, was measured to be between 50-70 mPas, which is acceptable.

FIG. 3 illustrate the gel strength of samples 1-12 after addition of 7.5 ml calcium carbonate. Similar to the test with lower added calcium carbonate (5 ml), the inventors found that the samples 2, 5 and 8 exhibit the highest gel strength (when leaving out sample 13).

Of all combinations sample 2, 5 and 8 result in the highest gel formation with or without added calcium.

Perfect Fit® has a very positive effect on the suspension as shaking and/or stirring the first mixture for about 15 to 60 seconds created an aqueous diet product that was clear and overall without sedimentation and lumps.

Viscosity of Alginate Combinations with Erythritol and Calcium Carbonate

FIG. 4 show the viscosity of the all "ready to drink" alginate solutions shown in table 2 and 3 with erythritol, flavor and calcium carbonate of either 2 ml or 5 ml, 5% solution and pH of ~6.

With increased amounts of Protanal® GP5450 alginate in samples 20-22 the viscosity increases linear. Although, lower amounts of $CaCO_3$ for the samples 28-33, the inventors found a higher viscosity due to the alginate Manugel® DMB. When DMB is left out in samples 32+33 the viscosity decreases again.

However, in all cases it is evident that the viscosity of the majority of tested samples falls within the limits of the present invention as the viscosity ranges between 60-125 mPas.

As for Perfect Fit®, the suspension agent erythritol, had a very positive effect on the suspension of the different compositions when added to water, as shaking and/or stirring the preparation for not more than about 15 to 60 seconds created an aqueous diet product that was clear and overall without sedimentation and lumps.

Gel Strength of Alginate Combinations from Table 2 and 3

FIG. 5 shows the measurement of gel strength by oscillatory shear rheology, from samples 20-34.

The highest gel strength was found for samples 20_A, 21_A and 22_A which also had the highest calcium added (5 ml of 5% $CaCO_3$). When lowering calcium content the inventors observed a radical decrease in gel strength for these samples (20-22). Samples 28-31 exhibit higher gel strength with the alginate Manugel® DMB compared to samples 32+33 without Manugel® DMB.

Gel Strength of Alginate Combinations from Table 4

Table 5 shows the measurement of gel strength by oscillatory shear rheology, from samples 35-39.

TABLE 5

| Sample | Gel Strength (Pa) |
|---|---|
| 35 | ~1500-1600 |
| 36 | ~1200-1285 |
| 37 | ~1085 |
| 38 | ~1050 |
| 39 | ~1550-1650 |

As can be seen in table 5, the highest gel strength was found for sample 39. On this basis it was estimated that the combination of 1.45 g Manugel® GMB; 1.45 g Manugel® GHB, 1.5 g Protanal® GP1740, 0.25 g Protanal® LF 5/60, 0.5 g Protanal® GP5450 and 3 g erythritol provided an optimal balance of solubility and viscosity before and after gel formation, resilience of the gel, water retention capacity and reversal time for gel formation.

However, this selection should not be regarded as limiting for the invention, and it is contemplated that other alginates may also be used within the scope of the invention or that other combinations of different alginates may likewise be employed.

What is claimed is:

1. A diet product comprising a composition in the form of a reconstitutable powder comprising a calcium salt, at least one low viscosity alginate having a viscosity of less than 100 mPaS in a 1 wt % aqueous solution, and at least one high viscosity alginate having a viscosity of more than 100 mPaS in a 1 wt % aqueous solution, wherein the low viscosity alginate is selected to be one that does not form a gel in the presence of calcium ions at pH 7, wherein the calcium salt has a solubility of at least 5 mg per ml at 20° C. and pH 7, wherein the weight of the alginates in the aqueous diet product is between 0.5 wt % and 1.6 wt %, and wherein the powder is readily soluble in water to form an aqueous product.

2. A diet product according to claim 1, wherein the at least one low viscosity alginate has a viscosity of less than 40 mPaS in a 1 wt % aqueous solution.

3. A diet product according to claim 1, wherein the composition comprises at least two low viscosity alginates and wherein at least one of said alginates has a viscosity below 40 mPaS in a 1 wt % aqueous solution.

4. A diet product according to claim 1, wherein the composition comprises at least three low viscosity alginates and wherein at least two of said alginates has a viscosity below 40 mPaS in a 1 wt % aqueous solution.

5. A diet product according to claim 1, wherein the composition comprises at least two high viscosity alginates.

6. A diet product according to claim 1, wherein the ratio of the weight of the at least one low viscosity alginate to the weight of the at least one high viscosity alginate in the composition is 1:1 to 10:1.

7. A diet product according to claim 1, wherein the composition further comprises at least one suspending agent in the form of a particulate material.

8. A diet product according to claim 7, wherein the at least one suspending agent is selected from the group consisting of erythritol, inulin, polydextrose, dextrin, oligofructose, and a combination of these.

9. A diet product according to claim 7, wherein the ratio of weight of the alginates to the suspending agent in the composition is 0.5:1 to 10:1.

10. A diet product according to claim 1, wherein the molecular weight of the alginates is 300,000 Da or below.

11. A diet product according to claim 1, wherein the ratio of beta-D mannuronic acid to alpha-L guluronic acid in the low viscosity alginates is equal to or below 1.

12. A diet product according to claim 1, wherein the ratio of beta-D mannuronic acid to alpha-L guluronic acid in the high viscosity alginates is equal to or above 1.

13. A diet product according to claim 1, wherein the composition further comprises between 0.1 and 20 wt % of the calcium salt based on the weight of the total composition.

14. A diet product according to claim 13, wherein the calcium salt is selected from the group consisting of calcium phosphate, calcium carbonate, calcium sulfate, calcium oxide, calcium citrate, calcium lactate, calcium chloride, calcium tartrate, and calcium malate.

15. A diet product according to claim 1, wherein the alginates have substantially no taste and no odor.

16. A diet product according to claim 1, wherein the weight of calcium salt in the aqueous product is between 0.1 wt % and 3 wt %.

17. A diet product according to claim 1, wherein the aqueous product has a viscosity that is either below 130 mPaS, below 110 mPaS or below 80 mPaS each calculated at a shear rate of 100 s$^-$, 20° C. and pH 7.

18. A diet product according to claim 1, wherein the viscosity of the aqueous product increases at least 50 times when the pH value is lowered from pH 7 to pH 2.

19. A diet product according to claim 1, wherein the viscosity of the aqueous product increases to at least 1200 PaS when the pH value is lowered from pH 7 to pH 2.

20. A diet product according to claim 1, wherein the gel weight obtained after the pH value is lowered from pH 7 to pH 2, is above 90 g/100 ml water.

21. A unit dosage of the composition defined in claim 1, wherein said unit dosage is intended for being dissolved in 500 ml water, and comprises between 2 and 8 g alginate.

22. A unit dosage according to claim 21, wherein the unit dosage further comprises 1.25 g calcium carbonate.

23. An aqueous diet product comprising the reconstitutable powder according to claim 1 and water.

24. A method for preparing an aqueous diet product which comprises-adding the powder composition according to claim 1 to a suitable volume of about 500 ml of water to form a mixture, and shaking and/or stifling the mixture for 15 to 60 seconds to create an aqueous diet product which is clear and overall without sedimentation and lumps.

25. A diet product of a composition in the form of a reconstitutable powder consisting essentially of: between 0.1 and 20 wt % of a calcium salt having a solubility of at least 5 mg per ml at 20° C. and pH 7; at least one low viscosity alginate which does not form a gel in the presence of calcium ions at pH 7 and having a viscosity of less than 100 mPaS in a 1 wt % aqueous solution; at least one high viscosity alginate having a viscosity of more than 100 mPaS in a 1 wt % aqueous solution; and at least one suspending agent selected from the group consisting of erythritol, inulin, polydextrose, dextrin, oligofructose, or a combination of these in an amount sufficient to assist in maintaining the calcium and alginate components in the solution; wherein the at least one low viscosity alginate and at least one high viscosity alginate are present at a weight ratio of above 1:1 to 10:1, and the weight of the alginates in the aqueous diet product is between 0.5 wt % and 1.6 wt %, wherein the composition has a solubility of at least 10 mg per ml water at 20° C. and pH 7 and forms an aqueous product when dissolved in water.

26. An aqueous diet product comprising the reconstitutable powder according to claim 25 and water.

27. A method for preparing an aqueous diet product, which comprises adding the powder composition according to claim 25 to a suitable volume of about 500 ml of water to form a mixture, and shaking and/or stifling the mixture for 15 to 60 seconds to create an aqueous diet product which is clear and overall without sedimentation and lumps.

\* \* \* \* \*

UNITED STATES PATENT AND TRADEMARK OFFICE
CERTIFICATE OF CORRECTION

Page 1 of 1

PATENT NO. : 9,023,828 B2
APPLICATION NO. : 14/123714
DATED : May 5, 2015
INVENTOR(S) : Larsen et al.

It is certified that error appears in the above-identified patent and that said Letters Patent is hereby corrected as shown below:

Title Page:
Item (75) Inventors, after "Finn Larsen, Hawick", delete "(DK)" and insert -- (UK) --.

In the Claims:
Column 18:
Line 2 (claim 17, line 4), delete "100 s⁻," and insert -- 100 $s^{-1}$, --.
Line 20 (claim 24, line 2), delete "comprises-adding" and insert -- comprises adding --.
Line 22 (claim 24, line 4), delete "stifling" and insert -- stirring --.
Line 49 (claim 27, line 4), delete "stifling" and insert -- stirring --.

Signed and Sealed this
Eleventh Day of August, 2015

Michelle K. Lee
*Director of the United States Patent and Trademark Office*